United States Patent [19]

Appel et al.

[11] Patent Number: 4,923,696

[45] Date of Patent: May 8, 1990

[54] METHOD TO PREPARE A NEUROTROPHIC COMPOSITION

[75] Inventors: Stanley H. Appel, Houston; McManaman, James L., Kingwood; Kenneth W. Vaca, Houston, all of Tex.

[73] Assignee: Baylor College of Medicine, Houston, Tex.

[21] Appl. No.: 179,229

[22] Filed: Apr. 22, 1988

Related U.S. Application Data

[60] Continuation-in-part of Ser. No. 46,134, May 4, 1987, abandoned, which is a continuation-in-part of Ser. No. 769,860, Aug. 23, 1985, abandoned, which is a division of Ser. No. 444,293, Nov. 24, 1982, abandoned.

[51] Int. Cl.$^5$ ............................................. A61K 37/02
[52] U.S. Cl. ..................................... 424/548; 514/21; 514/885; 530/350; 530/841; 530/326
[58] Field of Search .................... 514/21, 885; 424/95; 530/351, 841, 326

[56] References Cited

FOREIGN PATENT DOCUMENTS

—082612 6/1983 European Pat. Off. .

OTHER PUBLICATIONS

Esch et al., PNAS U.S.A., vol. 82, (1985), pp. 6507–6511.
Gimenez-Gallego et al., Science, vol. 230, (1985), pp. 1385–1388.
Appel, Ann. Neurol., 10:499–505, (1981).
Smith and Appel, Science, 219:1079–1081, (1983).
Smith et al., J. Cell Biol., 101:1608–1621.
Vaca et al., Dev. Brain Res., 19:37–46, (1985).
Smith et al., J. Neurosci., 6(2):439–447, (1986).
McManaman et al., J. Biol. Chem., 263:5890–5897, (1988).

Primary Examiner—Jacqueline M. Stone
Attorney, Agent, or Firm—Davis Hoxie Faithfull & Hapgood

[57] ABSTRACT

The present invention is based on the discovery that amyotrophic lateral sclerosis (ALS), Parkinson disease and Alzheimer disease are due to lack of disorder-specific neurotrophic factors. Specific neurotrophic factors of ~20–22 kD and ~16–18 kD have been isolated from rat and human skeletal motor neurons, respectively, and purified. With tissue culture, the presence or absence of the specific neurotrophic factors provided herein can be assessed in ALS. If there is a deficiency, extracted and purified neurotrophic factors specific to the motor neuronal network or system can be administered to ALS-affected individuals.

29 Claims, No Drawings

METHOD TO PREPARE A NEUROTROPHIC COMPOSITION

CROSS-REFERENCE TO RELATED APPLICATIONS

The present application is a continuation-in-part of U.S. Ser. No. 046,134, filed May 4, 1987, which is a continuation-in-part of U.S. Ser. No. 769,860, filed Aug. 23, 1985, which is a divisional of U.S. Ser. No. 444,293, filed Nov. 24, 1982, all now abandoned.

FIELD OF THE INVENTION

The field of the invention is a method to prepare neurotrophic factors for the treatment of amyotrophic lateral sclerosis disease.

BACKGROUND OF THE INVENTION

The causes of some of the most common and most devastating diseases of the nervous system remain unknown. Prominent on this list are amyotrophic lateral sclerosis (ALS), parkinsonism, and Alzheimer disease. Each of these conditions is presently considered to be a degenerative disorder of unknown origin. In each, viral or immunological causes have been suggested, but no convincing reproducible data support the presence of an infectious agent or a cell-mediated or humoral immune factor. All three diseases reflect pathological change in a relatively limited network within the peripheral or central nervous system, or both.

Amyotrophic Lateral Sclerosis

Amyotrophic lateral sclerosis is the name given to a complex of disorders that compromise upper and lower motor neurons. Patients may present with progressive spinal muscular atrophy, progressive bulbar palsy, primary material sclerosis, or a combination of the conditions. The majority of patients have components of all three types, but each form may represent the sole clinical manifestation of motor system involvement [1]. (Reference numbers are to references listed at the conclusion of the "Background of the Invention"). At the present time in the United States, the incidence of the combined disease is approximately 1.8 per 100,000 [2] and its prevalence is between 5 and 7 per 100,000. Males are affected more commonly than females, the ratio of males to females being 1.6:1. Approximately 10% of the cases are familial [3]. Onset may occur at any age but is most common in the later decades, and the incidence appears to increase with age. The mean age of onset is 66 years [6].

Distal weakness and atrophy are the hallmarks of the disorder, and both upper and lower motor neurons are affected. Sensory signs are usually absent, although quantitative sensory assessment by electromyography may indicate abnormalities [4]. The extraocular muscles and bladder are rarely involved. Progression usually occurs over 12 to 30 months, and death ensues as a result of severe impairment of breathing functions.

The major pathological abnormality is loss of large motor neurons of the motor cortex, brain stem, and spinal cord. In the remaining motor neurons there is chromatolysis and inclusions that are rich in ribonucleic acid or are Lewy body-like or eosinophilic (Bunina bodies) [5]. The whole neuron seems to be involved, and there is only minimal evidence of "dying back" of the peripheral axons [6]. In addition, large proximal axonal swellings (spheroids) have been reported in motor neurons from patients with ALS [7], and similar abnormalities can be induced in animals following injection of B-B'-iminodiproprionitrile, with resulting impairment of slow axonal transport [8]. These spheroids represent abnormalities of neurofilaments and may be found in the cytoplasm as well as in the axon.

Involvement of the motor system has been described in familial conditions appearing at earlier ages [3]. For example, Werdnig-Hoffman disease present in utero or in infancy as a rapidly progressive autosomal recessive condition characterized by severe weakness. Kugelberg-Welander disease is first seen in the juvenile period with weakness in the hips and subsequent involvement of the shoulder muscles. It is also inherited as an autosomal recessive disorder, although autosomal dominant and X-linked recessive transmission have been described Both of these clinical conditions result from anterior horn cell abnormalities and share clinical features with the progressive muscular atrophies appearing later in life.

The following references are relevant to the invention:

1. Munsat T. L., Bradley W. G.: Amyotrophic lateral sclerosis In Tyler H. R., Dawson D. M. (eds): Current Neurology, vol 2. Boston, Houghton Mifflin, 1979
2. Juergens S. M., Kurland L. T., Okazaki H., Mulder D. W.: ALS in Rochester, Minn., 1925–1977. Neurology (N.Y.) 30:463–470, 1980.
3. Engel W. K.: Motor neuron disorders. In Goldensohn E. S., Appel S. H. (eds): Scientific Approaches to Clinical Neurology. Philadelphia, Lea & Febiger, 1977, pp 1322–1346
4. Dyck P. J., Stevens J. C., Mulder D. W., et al: Frequency of nerve fiber degeneration of peripheral motor and sensory neurons in amyotrophic lateral sclerosis: morphometry of deep and superficial peroneal nerve. Neurology (Minneap) 25:781–785, 1975
5. Chou S. M.: Pathognomy of intraneuronal inclusion in ALS. In Tsubaki T., Toyokura Y. (eds): Amyotrophic Lateral Sclerosis. Tokyo, University of Tokyo Press, 1979, pp 135–176
6. Bradley W. G., Kelemen J., Adelman L. S., et al: The absence of dying-back in the phrenic nerve of amyotrophic lateral sclerosis (ALS). Neurology (N.Y.) 30:409, 1980
7. Carpenter S.: Proximal axonal enlargement in motor neuron disease. Neurology (Minneap) 18:841–851, 1968
8. Griffin J. W., Hoffman P. N., Clark A. W., Carroll P. T., Price D. L.: Slow aonal transport of neurofilament proteins: impairment of beta, beta-iminodipropionitrile administration. Science 202: 633–635, 1978

The following additional references are also relevant to the invention: Bottenstein J. E., Sato G. H.: Growth of a rat neuroblastoma cell line in serum-free supplemented media Proc Natl Acad Sci U.S.A. 76:514–517, 1979

Bradshaw R. A.: Nerve growth factor. Annu Rev Biochem 47:191–216, 1978

Brown M. C., Holland R. L., Hopkins W. G.: Motor nerve sprouting. Annu Rev Neurosci 4:17–42, 1981

Cohen J. Levi-Montalcini R.: A nerve growth-stimulating factor isolated from snake venom. Proc Natl Acad Sci U.S.A. 42:571–574, 1956

Davies P.: Loss of choline acetyltransferase activity in normal aging andi n senile dementia Adv Exp Med Biol 113:251–257, 1978

Finch C. E.: Catecholamine metabolism in the brains of aging male mice. Brain Res 52:261–276, 1973

Fonnum F.: Radiochemical micro assays for the determination of choline acetyltransferase and acetycholinesterase activities. Biochem J 115:465–472, 1969

Giller E. L., Neale J. H., Bullock P. N., Schrier B. K., Nelson P. G.: Choline acetyltransferase activity of spinal cord cell cultures increased by co-culture with muscle and by muscle-conditioned medium. J Cell Biol 74:16–29, 1977

Hemmendinger L. M., Garber B. B., Hoffman P. C., Heller A.: Target neuron-specific process formation by embryonic mesencephalic dopamine neurons in vitro. Proc Natl Acad Sci U.S.A. 78:1264–1268, 1981

Hollyday M., Hamburger V.: Reduction of the naturally occurring motor neuron loss by enlargement of the periphery J Comp Neurol 170:311–320, 1976

Hudson A. J.: Amyotrophic lateral sclerosis and its association with dementia, parkinsonism and other neurological disorders: a review. Brain 104:217–247, 1980

Johnson D. A., Pilar G.: The release of acetylcholine from post-ganglionic cell bodies in response to depolarization. J Physiol (Lond) 299:605–619, 1980

Mobley W. C., Server A. C., Ishii D. N., Riopelle R. J., Shooter E. M.: Nerve growth factor. N Engl J Med 297:1096–1104, 1977

Pestronk A., Drachman D. B., Griffin J. W.: Effects of aging on nerve sprouting and regeneration. Exp Neurol 70:65–82, 1980

Pittman R. W., Oppenheim R. W.: Neuromuscular blockage increases motoneurone arrival during normal cell death in the chick embryo. Nature 271:364–366, 1978

Prochiantz A., DiPorzio U., Kato A., Berger B., Glowinski J.: In vitro maturation of mesencephalic dopaminergic neurons from mouse embryos is enhanced in presence of their striatal target cells. Proc Natl Acad Sci U.S.A. 76:5387–5391, 1979

Reed D. M., Torres J. M., Brody J. A.: Amyotrophic lateral sclerosis and parkinsonian-dementia on Guam, 1945–1972. Am J Epidemiol 101:302–310, 1975

Smith R. G., Appel S. H.: Evidence for a skeletal muscle protein that enhances neuron survival, neurite extension, and acetylcholine (ACh) synthesis. Soc Neurosci Abstr 11:144, 1981

U.S. Pat. No. 4,294,818 discloses a diagnostic method for multiple sclerosis comprised of antibody preparations reactive with antigenic substances associated with lymphocytes.

U.S. Pat. No. 3,864,481 discloses a synthetic amino acid for suppression and diagnosis of multiple sclerosis.

U.S. Pat. Nos. 3,961,894; 4,046,870; and 4,225,576 disclose assay techniques for detecting hormones in the body.

SUMMARY OF THE INVENTION

The present invention is based upon the discovery that amyotrophic lateral sclerosis results from lack of a neurotrophic hormone specific for the neuronal network or system which is elaborated or stored in the synaptic target of the affected neurons and exerts a specific effect by acting in a retrograde fashion. Diagnosis and treatment of ALS are based on motor neurotrophic factors which are extracted from skeletal muscle tissue and tested for enhancement of motor neuron survival, and cholinergic and morphological differentiation in cultures of motor neurons. The extracted and assayed neurotrophic factors are then purified. In case deficiencies, neurotrophic factors specific to the particular motor neuronal network or system are administered to individuals suffering from ALS.

Accordingly, it is an object of the present invention to provide a composition effective for the treatment of ALS.

It is a further object of the present invention to treat ALS by administering a neurotrophic factor specific to the motor neural system.

A further object of the present invention is the extraction and purification of a neurotrophic factor with an apparent molecular weight of 20–22 kD, as measured by SDS-PAGE analysis, and a pI of 4.8, which factor is specific for the motor neuronal system.

Yet another aspect of the invention is the extraction and purification of a neurotrophic factor with an apparent molecular weight of ~16–18 kD, as measured by SDS-PAGE, and a pI of 9, which factor is also specific for the motor neuronal system.

Other and further objects, features and advantages of the invention are set forth throughout the specification and claims.

DESCRIPTION OF PRESENTLY PREFERRED EMBODIMENTS

From the foregoing, ALS can be seen to represent a disorder of specific neuronal networks, that is, the motor neuronal system. This disorder reflects changes in a presynaptic neuronal input with secondary alterations of the target tissue. ALS represents pathological change in Betz cells, cranial motor neurons, and anterior horn cells.

The role of neurotrophic factors of the present invention is a modification of the notion of intrinsic aging of selected neurons; that is, the presence of specific extrinsic factors influence the maintenance and survival of neurons. In each disease, the system de9eneration is due to diminished availability of a specific neurotrophic factor normally released by the post-synaptic cell, taken up by the presynaptic terminal, and exerting its effect by retrograde transport up the presynaptic axon to the soma and nucleus.

Thus, in the motor neuronal systems, neurotrophic proteins are present in vitro which enhance neuron survival, promotes neurite extension, and increase the activity of the neurotransmitter synthetic enzymes in the innervating cell. The same factors responsible for survival of neurons in vitro may also be responsible for survival of neurons in vivo. Similar or even the same factors may also be responsible for maintenance of neurons throughout the life cycle in vivo, and may decrease as a normal function of aging.

Thus, a primary manifestation of ALS disease is failure of the target tissue to supply the necessary neurotrophic factor. Marked pathological change in the tissue need not be present. Impaired synthesis or release (or both) of the relevant factor would represent the sine qua non of disease. For example, in the lower motor neuron syndromes of ALS, failure of muscle cells to release the appropriate motor neurotrophic factor would result in failure of anterior horn cells. The pathological picture would be one of gradual cessation of anterior horn cell function with chromatolysis and of altered nuclear function with minimal evidence of "dying back." Similarly, impairment of Betz cells would result from decreased release of neurotrophic factor from target neurons. A more precise statement is not possible for the upper motor neuron syndrome since the synaptic target of the descending Betz cell axon is not known with certainty in humans.

Thus, in this system, the lack of an appropriate factor released from post-synaptic cells impairs the viability of the presynaptic cells, anterior horn cells and Betz cells will undergo gradual deterioration. With the availability of tissue culture, the presence, deficiency, or absence of specific neurotrophic factors can be assessed in ALS disease readily and easily.

The present invention discloses a method to prepare a protein composition effective in treating amyotrophic lateral sclerosis comprising:

(a) extracting proteins from the skeletal muscle of a normal mammal; and (b) assaying the protein isolate for trophic effects on motor neurons.

The method of the present invention further comprises the isolation and purification of a protein fraction having an apparent molecular weight in the range of about 20,000 to about 22,000 daltons as measured by SDS-polyacrylamide gel electrophoresis (SDS-PAGE) and a protein fraction having an apparent molecular weight in the range of about 16,000 to about 18,000 daltons as measured by SDS-PAGE. The molecular weight ranges of the factors described herein have been determined for both in solution by gel filtration chromatography and by SDS-PAGE analysis. As is generally recognized in the art, the specific molecular weight of the claimed neurotrophic factors may vary according to the procedure used to isolate the proteins. As used herein, the ~28 kD factor isolated using gel filtration chromatography corresponds to the ~20-22 kD factor isolated by SDS-PAGE. The ~12 kD neurotrophic factor isolated using gel filtration chromatography corresponds to the protein composition with a molecular weight range of about 16,000 to about 18,000 daltons as determined by preparative SDS gel electrophoresis.

By "trophic effects" it is meant that the extracted neurotrophic factors have selective effects on specific neural elements which contribute to the survival, growth, maturation, and regeneration of neurons present in the nervous tissue.

Biological assays for cholinergic activity are used as one means of demonstrating the trophic effects possessed by the present neurotrophic factors. Cholinergic activity is usually defined as the ability to stimulate the synthesis of acetylcholine or alternatively, as the ability to increase the levels of the enzyme choline acetyltransferase.

Very generally, the isolated motor neurotrophic factors which exhibit trophic effects on motor neurons can be isolated from skeletal muscle taken from a variety of normal mammals. For example, skeletal muscle from human, rat and bovine species have all yielded a protein fraction with an identifiable neurotrophic factor. It has been found that a neurotrophic factor isolated from rat skeletal muscle has a molecular weight in the range of ~28 kD as determined in solution by gel filtration chromatography, and an isoelectric point of about 5.1 as determined by preparative chromatofocusing chromatography. This particular factor has been further purified by SDS-polyacrylamide gel electrophoresis and the apparent molecular weight is ~20-22 kD. Isoelectric focusing using the SDS-PAGE-purified material provides an isoelectric point of about 4.7. Thus, the isoelectric point of the ~20-22 kD neurotrophic factor is given at pH $5 \pm 0.5$ since both of the determined isoelectric points are within experimental error.

It has also been found that a neurotrophic factor isolated from human skeletal muscle has a molecular weight of about 12 kD as determined in solution by gel filtration chromatography, a molecular weight of about 16-18 kD as determined by SDS-PAGE analysis, and an isoelectric point of about $9 \pm 1.0$ as determined by preparative chromatofocusing chromatography.

It is within the scope of this invention to extract, assay and purify other neurotrophic factors present in muscle by one skilled in the art using the techniques disclosed herein and further that the ~20-22 kD factor from rat skeletal muscle can also be isolated from muscle of other mammalian species including human. In accord, the ~17 kD factor from human skeletal muscle can also be isolated from muscle of other mammalian species including rat.

The neurotrophic factors described herein can be isolated using a variety of conventional and well-known extraction and purification procedures. Extraction procedures include sonicating the skeletal muscle tissue in an aqueous solution using a blender or laboratory homogenizer. The aqueous solution is usually buffered to physiological salt and pH and may contain one or more protease inhibitors including one or more chelating agents. The particular buffers, chelating agents, and protease inhibitors used in the extraction step are not critical to practice the present invention; thus, the following reagents are merely illustrative of the reagents which might be utilized. For example, the aqueous solution may include phosphate-buffered saline solution (PBS), citrate-phosphate buffer; chelating agents may include EDTA, EGTA, and the like; and protease inhibitors may include phenylmethylsulfonyl fluoride (PMSF), pepstatin A, bacitracin, leupeptin, Nα-p-tosyl-L-arginine methyl ester (TAME), and Nα-benzoyl-L-arginine ethyl ester (BAEE). The factors described in these examples are stable at moderate acid and basic pHs. Therefore, extraction could be in acidic or basic aqueous solutions such as acetic acid or ethanolamine solutions. A preferred embodiment of the present invention utilizes PBS, pH 7.4, supplemented with EDTA, EGTA, PMSF, and pepstatin A to extract the ~20-22 kD muscle neurotrophic factor. Alternatively, a preferred embodiment used to extract the ~17 kD neurotrophic factor includes PBS, pH 7.4, supplemented with EDTA, EGTA, acetic acid and PMSF. Muscle extracts prepared by this tissue homogenization are then clarified by centrifugation.

Several types of useful purification procedures are size fractionation using molecular sieve chromatography, ion exchange chromatography under suitable conditions; affinity chromatography using for example, antibodies directed to the biologically active form of the neurotrophic factor; absorption chromatography using non-specific supports, such as hydroxyapatite, silica, alumia, and so forth; and also gel-supported electrophoresis. A detailed description of the procedures used to purify the present neurotrophic factors is described in the examples below.

The ~20-22 kD neurotrophic factor may be purified by adjusting the supernatant to pH 5 with acetic acid and collecting the resultant precipitate by centrifugation.

The resultant protein pellet obtained from the acetic acid precipitation may be further purified by any of a number of chromatography procedures including, for example, gel filtration chromatography, hydroxylapatite chromatography, anion or cation exchange chromatography, heparin affinity chromatography, and SDS-polyacrylamide gel electrophoresis. The procedures may be used individually or sequentially to purify the desire neurotrophic factors; however, a preferred embodiment of one purification scheme for the ~20–22 kD factor is described below.

The protein pellet from the acetic acid precipitation is resuspended in buffer and subjected to size fractionation by gel filtration chromatography using an appropriate matrix to resolve proteins in the 25–31 kD range. The column is equilibrated and run with an appropriate buffer such as 10 mM ethanolamine, 150 mM NaCl, 0.01% polyethylene glycol (PEG); pH 9.2, at 4° C. Polyethylene glycol in the range of 0.01% to about 0.1% is included in all buffer solutions used subsequent to the initial extraction and precipitation steps as PEG has been found to markedly increase the recovery of the ~20 –20–22 kD cholinergic neurotrophic factor activity during purification. The apparent molecular weight of the neurotrophic factor from gel filtration chromatography is estimated at 28–30 kD.

The eluate is pooled and concentrated by loading directly onto hydroxylapatite equilibrated in the same buffer. The cholinergic trophic activity is step-eluted from hydroxylapatite using 20 mM sodium phosphate in the equilibrium buffer.

Next, the eluted factor is further purified by anion exchange chromatography. The eluant from the previous hydroxylapatite step is diluted 1:5 in a low salt buffer and adjusted to pH ~7 5. Usually, a low salt buffer such as 25 mM HEPES is used. This solution is adjusted to pH 7.5 and adsorbed to an anion exchange column such as DEAE cellulose equilibrated with a similar buffer containing 30 mM NaCl and 0.01% PEG; pH 7.5. This column is eluted with a linear gradient of NaCl from 0.03 M to 0.3 M in the same buffer. The neurotrophic activity elutes between about 0.15 M NaCl and 0.2 M NaCl.

The active ~20–22 kD cholinergic neutrotrophic factor may be concentrated and further purified by an additional hydroxylapatite chromatographic step. The active DEAE eluant is adjusted to pH 7 with acetic acid and applied to a hydroxylapatite column equilibrated with 25 mM HEPES buffer, 0.01% PEG; pH 7. At this pH, all of the activity remains bound to hydroxylapatite. The column is washed with the same buffer and then sequentially step-eluted using 20 mM sodium phosphate, followed by 30 mM and 40 mM sodium phosphate in 25 mM ethanolamine, 0.01% PEG, pH 9.2. The neurotrophic factor may be concentrated by ultrafiltration.

Final purification may be achieved by preparative SDS-PAGE under non-reducing conditions. Most of the activity migrates with an apparent molecular weight of 20–22 kD, however in some preparations, a small amount of activity migrates at a slightly higher molecular weight of ~24–26 kD.

The purity of the neurotrophic factor may be further characterized by analytical SDS-PAGE. The molecular weight of the neurotrophic factor was not altered by acid treatment and exposure to reducing agents such as DTT, does not significantly alter the electrophoretic mobility of the ~20 band on the SDS-PAGE gels.

The apparent molecular weight of the y SDS-PAGE analysis is ~20–22 kD whereas the apparent molecular weight estimated by gel filtration chromatography is greater (~28 kD). These results support the molecular weight range provided for the present neurotrophic factor of 20–30 kD.

The isoelectric point of the ~20–22 kD cholinergic neurotrophic factor is determined bY preparative chromatofocusing chromatography following the procedure described by Pharmacia and incorporated herein by reference. The active fraction is eluted with pH 9–4 polybuffer (Pharmacia). Active fractions are found in the pH 4.7–5 fractions.

Preparative isoelectric focusing in agarose gels using pH 4 to 7 ampholines (Serva) was also used to estimate the isoelectric point of the active factor. Using this technique, the activity was recovered between pH 4.8 and pH 5.1. The isoelectric point of the SDS-PAGE purified material, determined by analytical isoelectric focusing using pH 4–6.5 Pagplates (LKB) was pH 4.8.

All steps above are carried out at 4° C. and fractions are stored at −80° C.

After each purification step, biological assays are performed to track activity and to determine the yield of the isolated protein component. In addition, biochemical assays can also determine the sensitivities of the muscle extracts to heat and proteases.

The amino acid composition of the SDS-PAGE purified rat skeletal muscle neurotrophic factor was determined after 24 hr in 6N HCl at 150° C. and is shown in Table 1 below. The number of residues/mole of each amino acid is based on a molecular weight of 20 kD. In agreement with its acidic pI value, the factor is enriched in aspartic and glutamic acid residues. There are, however, also a significant number of lysine and arginine residues. Cysteine, tryptophan and methionine residues were not determined.

TABLE 1

| Amino Acid | Residues/mole (mean + range) |
|---|---|
| Aspartic Acid | 19 ± 1.0 |
| Threonine | 8 ± 0 |
| Serine | 14 ± 0.5 |
| Glutamic Acid | 28 ± 1.5 |
| Proline | 8 ± 0.5 |
| Glycine | 26 ± 1.0 |
| Alanine | 13 ± 0 |
| Valine | 11 ± 0 |
| Methionine | * |
| Isoleucine | 7 ± 0 |
| Leucine | 14 ± 0.5 |
| Tyrosine | 6 ± 0.5 |
| Phenylalanine | 8 ± 0.5 |
| Histidine | 10 ± 0.5 |
| Tryptophan | * |
| Lysine | 12 ± 0.5 |
| Arginine | 8 ± 0.5 |
| Cysteine | * |

*not determined ln addition to the determination of the amino acid composition, the purified neorotrophic factor has been cleaved by lysyl C peptidase (which specifically cleaves after lysine residues), and the following internal peptide has been identified and sequenced:

(K)-F-V-Y-A-T-C-N-F-T-L-L-E-L-N-N-A

The lysine residue bracketed by parentheses was not actually sequenced but its presence is assumed since lysyl C peptidase was used as the cleavage reagent.

The ~20–22 kD neurotrophic factor is assayed d from mammalian and on cultures of motor neurons obtaine avian species. It is preferred to use cultures of dissociated spinal cords obtained from E14 to E15 rat embryos. The biological activity of the molecule is based on the stimulation of survival, cholinergic, and morphological differentiation in these cultures. The preferred method of assay is to incubate cultures of rat motor neurons with the neurotrophic factor for 48 hours and measure stimulation of the level of choline acetyltransferase activity in each culture well. Assays employing survival, cell growth or the enhancement of other cholinergic properties in this and other types of motor neuron cultures can also be used to assay for this factor.

For the ~17 kD neurotrophic factor, the preferred method of the present invention comprises extracting proteins from human skeletal muscle by homogenizing muscle tissue in a buffer as described above for the ~20–22 kD cholinergic trophic factor. pBS is supplemented with 2 mM EDTA, 2 mM EGTA, 0.2 mM PMSF and made 0.5 M in acetic acid. After homogenization the extract is clarified by centrifugation. The ~17 kD cholinergic neurotrophic factor is then precipitated with ammonium sulfate. In practice, the precipitate which forms by adding ammonium sulfate to 100% of saturation is collected by centrifugation. The ~17 kD factor activity is found to precipitate at high ammonium sulfate concentrations (above 60% of saturation). Thus, an alternative to the later purification step is to remove material which precipitates at 60% ammonium sulfate saturation followed by collecting the precipitate which forms at 100% of saturation.

Next, the human neurotrophic factor is further purified by cation exchange chromatography. The ammonium sulfate pellet is resuspended in buffer (e.g., 40 mM sodium phosphate adjusted to pH 3.5 with 1 N HCl), stirred in the cold and clarified by centrifugation. The resulting solution is applied to a phosphocellulose (e.g., Cellex P) column equilibrated with the same buffer and after washing thoroughly, the neurotrophic factor is step eluted with the same buffer containing 1 M NaCl.

The human neurotrophic factor is further purified by gel filtration chromatography. The eluted factor is concentrated by ultrafiltration using, for example, an Amicon YM5 membrane and then applied to a gel filtration column capable of fractionating proteins in the 1500–30,000 dalton range. For example, a Sephadex G50 column equilibrated with PBS and 0.02% sodium azide may be used. The biological activity elutes over a broad range of fractions corresponding to 12–18 kD.

Lastly, the cholinergic neurotrophic factor is purified by heparin affinity chromatography. Active Sephadex fractions are applied to Heparin Affigel which is equilibrated with a buffer (e.g., 0.15 M HEPES) at pH ~7. Stepwise elutions are performed using the same buffer supplemented with 0.25 M, 0.5 M, 0.75 M, 1.0 M, 1.25 M, and 1.5 M NaCl. The majority of factor activity elutes in the 1.5 M NaCl step. However, significant activity has been observed in the flow-through fraction and may be collected. These fractions can be stored at −80° C.

Antisera raised against purified recombinant basic fibroblast growth factor (FGF) was used to further evaluate and characterize the human neurotrophic factor. All the neurotrophic activity of both the heparin-bound material and the flow-through from the heparin column was completely neutralized at a 1% dilution of the antibody. These results indicate that the neurotrophic activity isolated from human muscle factor is basic FGF or an antigenically related compound.

The isoelectric point of the ~17 kD cholinergic neurotrophic factor was determined by preparative chromatofocusing chromatography following the procedure described by Pharmacia. The active fraction is eluted with Polybuffer 96 (Pharmacia) and the activity is found in the pH 9 fraction.

Biological assays are performed after each purification step to track activity and to determine protein yield as discussed earlier with respect to the isolation of the ~20–22 kD neurotrophic factors. The particular assays performed on the human neurotrophic factor differ slightly from those used in the rat muscle examples and are described below.

The ~17 kD neurotrophic factor is assayed on cultures of motor neurons obtained from avian or mammalian species. It is preferred to use cultures of dissociated chick ciliary ganglion neurons obtained from E8 to E9 chick embryos as described by Vaca et al. Dev. Brain Res. (1985) 19:37–46. The biological activity of the factor is based on the stimulation of growth, survival, and cholinergic differentiation of cultured ciliary ganglion neurons. A preferred method of assay is to incubate the factor with dissociated chick ciliary ganglion cultures for 72 hours and measure the stimulation of the level of choline acetyltransferase activity. Assays employing survival, cell growth or the enhancement of other cholinergic properties in this, as well as in motor neuron cultures can also be used as assays for this factor.

If there is a deficiency of motor neurotrophic factor in an individual suffering from ALS, treatment is accomplished by administering any of the isolated neurotrophic factors described in the following examples.

The invention is further described by the following examples. These examples are not intended to limit the invention in any manner.

EXAMPLES

EXAMPLE 1

Preliminary Purification of Rat Neurotroohic Factors

Limb skeletal muscle (100 g) from 2-week-old Sprague-Dawley rats was homogenized in three volumes (wt/vol) of ice-cold PBS, pH 7.4, supplemented with 1 mM 0.5 mM EGTA, 1 mM PMSF, 0.1 µg/ml pepstatin A and 1 µg/ml of bacitracin, leupeptin, TAME, and BAEE, and centrifuged at 30,000×g for 1 hr at 4° C. to remove cellular debris. All centrifugations performed in the examples are run for 1 hr at 4° C. unless otherwise indicated. The resulting supernatant ($S_1$) was recentrifuged at 130,000×g for an additional hour and the resulting supernatant (crude extract) was adjusted to pH 5 with 1 M acetic acid and stirred on ice for 30 minutes. Precipitated protein was collected by centrifugation at 30,000×g for 1 hour. The collected precipitate was reextracted in 100 ml EBS (10 mM ethanolamine, 150 mM NaCl, 0.01% PEG, pH 9.2) and centrifuged at 30,000×g for 1 hour. The clear supernatant (pH 5-S) containing the CAT-development (CDA) activity was then subjected to gel permeation chromatography.

EXAMPLE 2

Gel Filtration and Hydroxylapatite Chromatography

The pH5-P was resuspended in 25 mM ethanolamine, 0.01% PEG, pH 9.2 and applied to Sephadex G-100 (Pharmacia) equilibrated with EBS at 4° C. CAT-development activity elutes between 15 and 45 kD;

these fractions were pooled and applied directly to a 1×6 cm column of hydroxylapatite (Bio-Rad, Richmond, Calif.) equilibrated with EBS. The minor peak of activity in the void volume, eluted at a higher molecular weight of >50 kD, was stored frozen at −80° C. without further purification. All of the CAT-development activity was retained and was quantitatively eluted from hydroxylapatite with a step-gradient of 20 mM $NaH_2PO_4$ in the equilibrium buffer (HAP-9). This procedure rapidly concentrates CAT-development activity.

EXAMPLE 3 and Hydroxylapatite Chromatography and Hydroxylapatite Chromatography

The CAT-development activity from the HAP-9 eluent was diluted 1:5 with 25 mM HEPES, pH 7.5, and applied to a 1.5×20 cm column of DEAE cellulose equilibrated with 25 mM HEPES, 0.03 M NaCl, and 0.01% PEG, pH 7.5. All of the CAT-development activity bound to DEAE cellulose at pH 7.5 and was eluted from the DEAE cellulose with a linear gradient of 0.03 M to 0.3 M NaCl. The CAT-development activity elutes between 0.15 M and 0.2 M NaCl. These active DEAE fractions were pooled, adjusted to pH 7 with 1.0 M HCl and applied to a 0.9×3 cm column of hydroxylapatite equilibrated with 25 mM HEPES buffer and 0.01% PEG, pH 7.0. After washing the column with the equilibration buffer supplemented with 20 mM $NaH_2PO_4$, the CAT-development activity was sequentially step-eluted with 30 ml of 20 mM $NaH_2PO_4$ followed by 30 ml each of 30 mM $NaH_2PO_4$ and 40 mM $NaH_2PO_4$ in 25 mM ethanolamine and 0.01% PEG, pH 9.2. The 30 mM $NaH_2PO_4$ eluant (HAP-7) was concentrated to 0.1 ml in two steps by ultrafiltration using Amicon YM-5 membrane, followed by a Centricon-10 membrane. The concentrated material was used for preparative polyacrylamide gel electrophoresis. A summary of the purification results for the ~20–22 kD cholinergic factor is provided in Table 2.

C. in 1.0 ml of 25 mM HEPES, 0.01% PEG, pH 7.5. The supernatants from gel slices were removed and stored at −80° C. Most of the activity migrated with an apparent molecular weight of 20–22 kD, however, in some preparations a small amount of activity was observed migrating at a slightly higher molecular weight (~25kD). The recovery of proteins from SDS-PAGE by this method was estimated to be 80–85% based on the recoveries of [$^{125}$I]-Soybean trypsin inhibitor and [$^{125}$I]-labeled HAP-7 protein bands.

Analytical gels (0.5 mm thick) were prepared as described for the preparative gels, using a Bio-Rad mini-gel apparatus. The gels were run at 200 V for 45 minutes Prior to electrophoresis, samples were dried using a vacuum-centrifuge and resuspended in 10 μl of electrophoresis buffer. Boiled and reduced samples were resuspended in electrophoresis buffer containing 2 mm DTT and heated at 100° C. for 5 minutes before electrophoresis Following electrophoresis the gels were fixed in 10% acetic acid, 50% methanol and stained by the silver staining procedure of Oakley et al (1980) *Anal Biochem* 105:361–363. Gels containing iodinated were fixed and dried on Whatman No. 3 paper and exposed to Kodak X-OMAT RP-5 film at −70° C.

Pretreating the HAP-7 fraction with DTT prior to preparative SDS-PAGE did not significantly alter the migration position of the biological activity of the neurotrophic factor, nor lead to the appearance of additional activity migrating at a lower molecular weight. From 100 grams of skeletal muscle an average of 1100 units of activity were recovered in the 20–22 kD band from SDS-PAGE. This represents a 1.6% recovery from crude extract and a 10% recovery of activity from the HAP-7 step.

EXAMPLE 5

Biological Assay for Rat Skeletal Muscle Neurotrophic Factor

The activity of the neurotrophic factor from rat skel-

TABLE 2

Summary of Purification Results

| Purification Step | Protein (mg) | Recovery | Sp. Act (Unit/μg) | Units | Purification | Recovery | Step Recovery |
|---|---|---|---|---|---|---|---|
| 100 KS | 4800 ± 602 | 100% | 50 | $2.4 \pm 1.9 \times 10^5$ | 1 × | 100% | |
| pH5P | 525 ± 140 | 11% | 286 | $1.5 \pm 1.1 \times 10^5$ | 3 × | 62% | |
| PH5S | 3249 ± 578 | 68% | 37 | $1.2 \pm 0.9 \times 10^5$ | 0.5 × | 50% | |
| G100$^{(B)}$ | 50 ± 22 | 1.0% | 1400 | $0.7 \pm 0.5 \times 10^5$ | 20 × | 29% | 47% |
| HAP-9 | 17 ± 6 | 0.3% | 1764 | $0.3 \pm 0.2 \times 10^5$ | 20 × | 12% | 43% |
| DEAE | 2.8 ± 1.2 | 0.06% | 10714 | $0.3 \pm 0.2 \times 10^5$ | 214 × | 12% | 100% |
| HAP-7 | 0.47 ± 0.05 | 0.01% | 23404 | $1.1 \pm 0.8 \times 10^4$ | 468 × | 4% | 37% |
| Preparative SDS | $4 \pm 1.7 \times 10^{-3}$ | 0.00012% | 275000 | $0.11 \pm 472 \times 10^4$ | 5500 × | 0.5% | 10% |

All the values, except those for SDS-PAGE, are averages based on extracting 100 grams of skeletal muscle of 2-week-old rats. The values for SDS-PAGE are the averages of 4 separate preparations.
$^{(B)}$From this point on, only further purification of pH5P is shown.

EXAMPLE 4

Preparative and AnalYtical SDS-PAGE

The HAP-7 fraction was subjected to preparative gel electrophoresis in 0.1% SDS under non-reducing conditions. Electrophoresis was performed according to Laemmli (1971) Nature (London) 277:680 using a 14% acrylamide −2.5% bisacrylamide separating gel (140×120×1 mm) and a 4.5% acrylamide stacking gel. Following electrophoresis the gel was rinsed once with 25 mM HEPES, pH 7.5 and sliced into 2 mm sections. Each section was minced, and extracted overnight at 4° etal muscle was assayed on dissociated cultures of 14-day embryonic rat spinal cord neurons. The spinal cord neurons were obtained from trypsin-dissociated spinal cords as described by McManaman et al., *Dev. Biol.* (1985) 112:248–252. The dissociated neurons were suspended in DMEM supplemented with 10% heat-inactivated horse serum and plated at a density of 100,000 cells/well in polylysine-coated 96-well microtiter plates. The cultures were preincubated for 1 hour at 37° C. in a humidified atmosphere of 90% air, 10% $COb_2$ to allow the neurons to attach to the substratum. The neurotrophic factor was added after the preincubation period Typically, 1 to 30 μl of this factor was added per well after the 1 hour preincubation period. The cells were incubated for an additional 48 hours at 37° C. as previously described, and then assayed for cholineacetyl transferase activity as described by Ishida and Deguchi, *J. Neuroscience* (1983) 3:1818–1823. The biological activity of this factor is based on the enhancement of CAT activity over control cultures treated with PBS. We have previously shown (McManaman et al. (1988) Dev Biol 125:311–320) that this assay is linear with respect to cell number and time of reaction and greater than 95% of the acetyltransferase activity in the cultures is inhibited by 10 μM NVP, a specific inhibitor of choline acetyltransferase, or by substituting carnitine for choline, or adding 4 units of AChE to the assay solution. The typical stimulations obtained with saturating amounts of this factor were 2 to 3-fold over control cultures. A unit of activity is operationally defined as a 50% stimulation of CAT activity over control cultures which are treated with an equal volume of sample buffer. Using this assay, an average of $5 \times 10^6$ units from 100 g of 14-day postnatal rat skeletal muscle was obtained.

The level of neurotrophic factor activity in crude extracts is dependent on the age of the animal. The highest specific activity was found in extracts of skeletal muscle from animals 12–15 days old. Although larger amounts of muscle could be obtained from older animals' muscle, 12 to 15 day old animals are preferred as the starting material for the purification of this factor because of the higher specific activity in this tissue.

EXAMPLE 6

Affinity of Rat Skeletal Muscle Factor for Lectins and Heparin

The possibility that the neurotrophic factor was glycosylated was investigated using specific lectin affinity columns. As shown in Table 3, only a small percentage of the $A_{280}$ material, and none of the neurotrophic factor-activity in the active fraction from the HAP-9 step, bound to affinity columns composed either of concanavalin A, wheat germ, or Limulus lectins, although each of these columns bound control glycoproteins well.

The ability of the neurotrophic activity in the pH 5-P fraction to bind heparin was analyzed using a heparin-Sepharose affinity column. As shown in Table 3, at this stage of the purification only 8% of the protein, and none of the trophic activity, bound heparin-Sepharose. Similar data was also observed when the DEAE-fraction containing the biological activity was analyzed by heparin-Sepharose chromatography.

Approximately 2,000–3,000 units of the rat skeletal muscle factor were individually applied to each of the columns in Table 3. The values presented therein are the percentages of applied activity and protein which were recovered in the flow-through plus wash or in the sugar or salt eluants.

The data presented in the afore-described examples, including the amino acid sequence information, the isoelectric point and the absence of cross-reaction with antibodies to basic FGF, demonstrate that this factor is a novel cholinergic factor unrelated to FGF.

TABLE 3

Affinity of Rat Muscle Factor for Lectins and Heparin

| | | % of Applied (± SD) | | | |
|---|---|---|---|---|---|
| | | Protein | | Protein | |
| Type of Column | Eluting Agent | Non-Retained | Retained | Non-Retained | Retained |
| Concanavalin A | α-Methaylmannopyranoside | 95 ± 2 | 5 ± 2 | 95 ± 8 | ND* |
| Triticum vulgaris | n-Acetylglucosamine | 98 ± 3 | ND | 97 ± 7 | ND |
| Limulin | n-Acetylneuroaminic acid | 96 ± 4 | 3 ± 2 | 95 ± 6 | ND |
| Heparin | 5 M NaCl | 95 ± 3 | 4 ± 1 | 96 ± 8 | ND |

*ND = not detected

EXAMPLE 7

Human Muscle Preparation

Iliopsoas, pectoral muscle, or both muscle sources were obtained within less than 20 hr postmortem, usually from acute trauma victims. About 0.4–0.5 kg of muscle was processed for a single preparation. After tendon and fat were removed, the remaining tissue was cut into small pieces and homogenized in a 1 liter PBS solution (pH 7.4) supplemented with 2 mM each EDTA and EGTA, 0.2 mM PMSF, and 0.5 M acetic acid with a Waring blender. The homogenate was centrifuged at 27,000 g for 1 hr and the supernatant was decanted through several layers of cheesecloth. The active protein fraction was precipitated by adding ammonium sulfate to 100% saturation and collected by centrifugation at 27,000 g for 1 hr.

The pellet was resuspended in 250 ml of 40 mM $NaH_2PO_4$, adjusted to pH 3.5 with 1 N HCl, and stirred for 30 min in the cold. This solution was centrifuged at 100,000 g for 1 hr and the pellet discarded. The supernatant was diluted with distilled water to a conductivity of 25 mS/cm.

Ion-exchange chromatography was performed by adding about 200 ml of a Cellex P (Bio-Rad) slurry to the diluted supernatant in resuspension buffer, and the mixture was stirred overnight in the cold. The Cellex P and bound protein was collected on filter paper with a Buchner filter, rinsed with the resuspension buffer, and then resuspended in a beaker containing 250 ml of the resuspension buffer supplemented with 1 M NaCl. This solution was stirred 3 to 4 hours in the cold, after which the eluate was collected through a Buchner funnel. The filtrate was concentrated to approximately 5 ml on an Amicon YM5 filter.

The concentrate was chromatographed on a Sephadex G50 column (1.5×180cm pre-equilibrated with PBS with 0.02% NaN3). About 80 fractions of 100 drops or ~3 ml were collected. Most activity eluted at fractions 55–60 corresponding to ~17 kD. These fractions were pooled for further purification.

The pooled fractions were slowly applied to a Heparin Affi-gel column (Bio-Rad) according to the method of Kessler et al., *Proc Natl Acad Sci* (1986) 83:3528–3532. Bound proteins were eluted in several sequential steps using 0.5 M HEPES pH 7 buffer supplemented with 0.25 M, 0.5 M, 0.75 M, 1.0 M, 1.25 M and finally 1.5 M NaCl. Most of the cholinergic activity eluted around 1.5 M NaCl. However, a significant amount of activity was found in the flow-through fraction and was saved for future analysis A summary of purification results for the ~17 kD neurotrophic factor is provided in Table 4.

TABLE 4

Summary of Purification Results for Human Muscle Factor

| PURIFICATION STEP | TOTAL PROTEIN (by Pierce BCA Assay) | ESTIMATED YIELD (Total Units) (Based on CAT Activity) |
|---|---|---|
| 26,000 × g supernatant | 5.6–12.4 g | N.D. |
| 100,000 × g supernatant | 430–750 mg | 38,000 (1 estimate) |
| Cellex P elute | 28–80 mg | 25–64,000 |
| G50 | 3.5–8.2 mg | 8–22,000 |
| Heparin 1.5 M | 5–30 μg | 1,200–3,000 |

Starting material 0.4–5 kg muscle (based on HMX 66–70).

EXAMPLE 8

Biological Assay for Human Skeletal Muscle Neurotrophic Factor

The human skeletal muscle factor was assayed on dissociated cultures of 8 to 9-day embryonic chick ciliary ganglion cultures. The cultures were prepared as described by Vaca et al. (1985), supra. Briefly, the ganglia were dissociated by trypsinization and suspended in Sato's medium, which was modified by substituting DMEM for standard salt solutions and by the addition of 0.4% heat-inactivated fetal calf serum. In a typical assay, the cells were plated in polylysine-coated 96-well plates at a density of ¼ to ⅓ ganglia per well and preincubated at 37° C. in 90% air, 10% $C_2$ in a humidified chamber for 1 hour. Neurotrophic factor (0.28% of the culture volume) was added after the preincubation period. The cells were then grown under the above conditions for 3 days, at which time they were assayed for cholineacetyl transferase activity as described by Fonmun, *J. Neurochem.* (1975) 24:407–409. Using the stimulation of CAT as the assay for neurotrophic activity, a unit was defined as a 50% stimulation over control cultures. Typically, 5 to 6 μg of trophic factor were obtained from 0.5 kg of autopsied human skeletal muscle.

The present invention, therefore, is well suited and adapted to attain the objects and ends and has the advantages and features mentioned, as well as others inherent therein.

While presently preferred embodiments of the invention has been given for the purpose of disclosure, changes can be made therein which are within the spirit of the invention as defined by the scope of the appended claims.

What is claimed is:

1. A method to prepare a neurotrophic protein composition which comprises:
   (a) extracting proteins from the skeletal muscle of a normal mammal;
   (b) assaying the protein extract for trophic effects on motor neurons; and
   (c) isolating protiens which are shown to exert a cholinergic effect on motor neurons.

2. The method of claim 1 which further comprises isolating a neurotrophic factor from the protein extract having said trophic effects, which factor has a molecular weight in the range of about 20,000 daltons to about 22,000 daltons as determined by SDS-PAGE analysis.

3. The method of claim 2 wherein said normal mammal is a rat.

4. The method of claim 2 wherein said protein fraction is isoelectric at a pH of 5±0.5.

5. The method of claim 2 wherein said neurotrophic factor has the internal peptide sequence: F-V-Y-A-T-C-N-F-T-L-L-E-L-N-N-A.

6. The method of claim 1 wherein said extraction comprises homogenizing the skeletal muscle in a buffered aqueous solution comprising one or more protease inhibitors.

7. The method of claim 6 wherein said aqueous solution comprises one or more chelating agents.

8. The method of claim 2 wherein said isolation comprises purifying the protein extract by adjusting the extract to pH 5 and collecting the precipitate.

9. The method of claim 8 wherein said isolation procedure comprises:
   (i) purifying the precipitate by gel filtration chromatography; and
   (ii) recovering an ~28 kD protein component.

10. The method of claim 8 wherein said isolation procedure further comprises:
    (i) fractionating the precipitate by hydroxylapatite chromatography; and
    (ii) eluting the bound protein to recover cholinergic factor activity.

11. The method of claim 8 wherein said isolation procedure further comprises:
    (i) separating the precipitate by anion exchange chromatography; and
    (ii) pooling the cholinergically active fractions to recover cholinergic factor activity.

12. The method of claim 9 wherein said purification procedure further comprises the steps of:
    (i) fractionating the ~28 kD protein component by hydroxylapatite chromatography;
    (ii) eluting the bound protein;
    (iii) separating the eluted protein by anion exchange chromatography;
    (iv) pooling the cholinergically active fractions;
    (v) fractionating the pooled activity by hydroxylapatite chromatography;
    (vi) recovering cholinergic factor activity; and
    (vii) concentrating the cholinergic factor activity using ultrafiltration.

13. The method of claim 12 wherein about 0.01% to about 0.1% polyethylene glycol is present in each chromatography step.

14. The method of claim 12 wherein said purification procedure further comprises subjecting the concentrated cholinergic factor activity to SDS-PAGE analysis and recovering a ~20–22 kD neurotrophic factor.

15. The method of claim 1 which further comprises isolating a neurotrophic factor from the protein extract having said trophic effects which factor has a molecular weight in the range of about 16,000 to about 18,000 daltons.

16. The method of claim 15 wherein said normal mammal is a human.

17. The method of claim 16 wherein said isolation procedure comprises adjusting the pH to 3.5 and adding ammonium sulfate to 100% saturation and collecting the resultant precipitate.

18. The method of claim 17 wherein said purification procedure further comprises:
    (i) fractionating the resultant precipitate by ion-exchange chromatography on phosphocellulose; and (ii) recovering bound protein with cholinergic factor activity.

19. The method of claim 17 wherein said purification procedure further comprises:
   (i) fractionating the resultant precipitate by gel filtration chromatography; and
   (ii) pooling the cholinergically active fractions corresponding to an ~17 kD factor to recover cholinergic factor activity.

20. The method of claim 17 wherein said purification procedure further comprises:
   (i) subjecting the resultant precipitate to heparin-affinity chromatography; and
   (ii) recovering cholinergic factor activity 21. The method of claim 18 wherein said purification procedure further comprises:
   (i) fractionating the recovered protein by gel filtration chromatography;
   (ii) pooling the cholinergically active fractions corresponding to an ~17 kD factor;
   (iii) subjecting the pooled fractions to heparin-affinity chromatography; and
   (iv) recovering an ~17 kD protein composition.

22. A protein prepared by the method of claim 2.

23. A substantially pure neurotrophic factor having a molecular weight of ~20,000 daltons and an soelectric point of 5±0.5, which contains an internal peptide sequence F-V-Y-A-T-C-N-F-T-L-L-E-L-N-N-A, and which is found in skeletal muscle.

24. The neurotrophic factor of claim 23 wherein a K residue precedes the first designated F residue.

25. A substantially pure neurotrophic factor having a molecular weight of between ~20,000 and ~22,000 daltons as measured by SDS FAGE, an isoelectric point of 5±0.5, which neurotrophic factor does not bind substantially to heparin, is substantially non-cross reactive with antibodies to basic PGF, and is found in skeletal muscle.

26. The substantially pure neurotrophic factor of claim 23 which is found in rat muscle tissue.

27. The substantially pure neurotrophic factor of claim 25 which is found in rat muscle tissue.

28. A substantaily pure neurotrophic factor having a molecular weight of between ~20,000 and ~22,000 daltons as measured by SDS PAGE, and an isoelectric point of 5±0.5, which neurotrophic factor does not bind substantially to heparin, is substantially non-cross reactive with antibodies to basic FGF, comprises the partial amino acid composition as follows:

| Amino Acid | Residues/mole (mean ± range) |
| --- | --- |
| Aspartic Acid | 19 ± 1.0 |
| Threonine | 8 ± 0 |
| Serine | 14 ± 0.5 |
| Glutamic Acid | 28 ± 1.5 |
| Proline | 8 ± 0.5 |
| Glycine | 26 ± 1.0 |
| Alanine | 13 ± 0 |
| Valine | 11 ± 0 |
| Isoleucine | 7 ± 0 |
| Leucine | 14 ± 0.5 |
| Tyrosine | 6 ± 0.5 |
| Phenylalanine | 8 ± 0.5 |
| Histidine | 10 ± 0.5 |
| Lysine | 12 ± 0.5 |
| Arginine | 8 ± 0.5 | and which is found in skeletal muscle.

29. The substantially pure neurotrophic factor of claim 28 which is found in rat muscle tissue.

* * * * *

UNITED STATES PATENT AND TRADEMARK OFFICE
CERTIFICATE OF CORRECTION

PATENT NO. : 4,923,696

DATED : May 8, 1990

INVENTOR(S) : Stanley H. Appel, et al

It is certified that error appears in the above-identified patent and that said Letters Patent is hereby corrected as shown below:

Column 7, line 18, replace "~20-20-22" with -- ~20-22 --.

Column 7, line 30, replace "~75" with -- ~7.5 --.

Column 7, line 65, after "of the" insert -- neurotrophic factor --.

Column 7, line 66, replace "y" with -- by --.

Column 8, line 66, after "assayed" insert -- on cultures of motor neurons obtained --.

Column 8, line 67, omit "d" before "from".

Column 8, line 67-68, omit "on cultures of motor neurons obtaine".

Column 10, line 44, replace "1 mM 0.5 mM" with -- 1 mM EDTA, 0.5 mM --.

Column 11, lines 13-14, replace "and Hydroxylapatite Chromatography and Hydroxylapatite Chromatography" with -- DEAE Chromatography and Hydroxylapatite Chromatography --.

UNITED STATES PATENT AND TRADEMARK OFFICE
CERTIFICATE OF CORRECTION

PATENT NO. : 4,923,696
DATED : May 8, 1990
INVENTOR(S) : Stanley H. Appel, et al.

It is certified that error appears in the above-identified patent and that said Letters Patent is hereby corrected as shown below:

Column 12, line 22, after "iodinated" insert -- proteins --.

Column 14, line 57, replace "NaN3" with -- $NaN_3$ --.

Column 15, line 33, replace "$C_2$" with -- $CO_2$ --.

Claim 23, column 17, line 26, after "daltons" insert -- as measured by SDS PAGE --;

Claim 23, Column 17, line 26, replace "soelectric" with -- isoelectric --.

Claim 25, column 17, line 34, replace "SDS FAGE" with -- SDS PAGE --.

Claim 25, column 18, line 1, replace "PGF" with -- FGF --.

Signed and Sealed this

Fifth Day of January, 1993

Attest:

DOUGLAS B. COMER

Attesting Officer

Acting Commissioner of Patents and Trademarks